United States Patent [19]

O'Lenick, Jr.

[11] Patent Number: 5,744,626
[45] Date of Patent: Apr. 28, 1998

[54] COMPLEX GUERBET ACID ESTERS

[75] Inventor: Anthony J. O'Lenick, Jr., Lilburn, Ga.

[73] Assignee: Lambent Technologies Inc, Norcross, Ga.

[21] Appl. No.: 807,909

[22] Filed: Dec. 26, 1996

Related U.S. Application Data

[63] Continuation-in-part of Ser. No. 548,737, Oct. 26, 1995, which is a continuation-in-part of Ser. No. 332,135, Oct. 31, 1994.
[51] Int. Cl.⁶ ..................................................... C07C 53/00
[52] U.S. Cl. ............................................ 554/227; 560/129
[58] Field of Search ............................... 554/227; 560/129

[56] References Cited

U.S. PATENT DOCUMENTS 4,425,458  1/1984  Lindner et al. .
4,868,236  9/1989  O'Lenick .

OTHER PUBLICATIONS

Morrison & Boyd, Organic Chemistry, 4th ed., p. 828, 1983.

Primary Examiner—Gary Geist
Assistant Examiner—Deborah D. Carr

[57] ABSTRACT

The present invention deals with the composition of matter and the utilization of certain novel complex esters which are prepared by the reaction of a guerbet acid and multi hydroxy compound like pentaerythritol.

9 Claims, No Drawings

5,744,626

COMPLEX GUERBET ACID ESTERS

RELATED APPLICATIONS

This application is a continuation in part of Ser. No. 548,737, filed Oct. 26, 1995 which is in turn a continuation in part of Ser. No. 332,135 filed Oct. 31, 1994.

BACKGROUND OF THE INVENTION

1. Field of the Invention

The present invention deals with novel, highly branched complex esters. The compounds are complex esters of multi hydroxy compounds like pentaerythritol reacted with guerbet acids. The introduction of the regiospecific branched guerbet acid portion of the molecule into the compounds of the present invention results in improved liquidity and mold release in polycarbonate applications.

As will become clear, we refer to the esters of the present invention as complex esters since the hydroxy compound used in the synthesis contains several hydroxyl groups, placed close to each other, resulting in branching in the ester, and the guerbet acid is itself branched in a very regiospecific beta branch.

2. Description of the Art Practices

Guerbet alcohols have been known for many years. Over the years there have been a number of derivatives patented. These materials can be oxidized into acids, which are raw materials for the preparation of the specific complex esters of the present invention. They possess the critical regiospecific guerbet linkage which when placed into complex esters results in unexpected improvements in both liquidity and mold release properties in polycarbonate.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

There are two different types of plastic lubricants. The mode of action and consequently the applications in which each type would be used differ considerably. External lubricants are insoluble in the polymer melt and as such have a tendency to form a mono-layer on the surface of the polymer. This results in a decrease in the friction between the metal and polymer. Such lubricants are referred to as mold release agents. Internal lubricants, on the other hand, are soluble in the polymer melt and as such have a tendency to promote flow of the polymer. These materials promote flow by reduction of internal stress and promotion of intermolecular slippage.

In order to have external lubricant properties the ester must be able to bloom to the surface of the plastic. Consequently, lower molecular weight materials make the best external lubricants. It is also known that there are certain blends of internal and external lubricants that result in synergistic interactions and particular improvements in plastic processing. The ability to modify the compounds used in plastic lubrication in terms of polarity and hydrophobicity allow for the tailor making of custom lubricants. This increases the flexibility of the formulator. The combination of two or more plastic lubricants into a combined system has been shown to result in a synergism between the materials in plastic lubrication. The ability to blend the different lubricants of this invention of varying polarities to give improved efficacy in blends is of major importance.

Polycarbonate compared to other thermoplastics is relatively high in viscosity and requires higher processing temperatures. Consequently, the use of lubricants with polycarbonate is particularly important in extrusion applications and in high performance injection molding applications. One of the large new growth areas for the use of polycarbonate in which lubrication is important is laser read compact recording discs. A superior grade of polycarbonate has been developed for this application and the presence of a mold release agent on the surface of the plastic has a very detrimental effect upon performance. The high performance lubricants of this invention are useful in this application.

Another new application area in which lubrication in polycarbonate is important is in the extrusion of polycarbonate sheets. In order to precision extrude these sheets to the tolerances required an effective lubricant agent is needed. Polycarbonate sheets are currently being evaluated as building materials for greenhouses. The esters of this invention are very useful in this application.

The use of polycarbonate to make products safe for food contact like water and other beverage bottles, microwave wear, baby formula bottles, beer mugs, pitchers, and food storage containers requires specialty high performance lubricants. Here again the deposition of mold release agent on the surface of the bottle would be highly undesirable, but the presence of an effective amount of a lubricant is very desirable to increase process efficiency and minimize rejected product.

To the extent that the foregoing patent is relevant to the present invention it is herein specifically incorporated by reference. Throughout the specification and claims, percentages and ratios are by weight, pressures are gauge and temperatures are Celsius unless otherwise noted.

THE INVENTION

This invention relates to the use of a particular group of regiospecific beta branched guerbet acids to prepare complex esters made by the reaction of a guerbet acid and a multi hydroxy compound to make a new series of unexpectedly efficient branched esters.

Esters are a class of compounds which find applications in many diverse segments of the chemical industry. One of the problems which is encountered using non-branched fatty acids to make complex esters is the fact that these materials are waxy solids with relatively high melting points. They possess some desirable mold release properties in polycarbonate, but are difficult to process.

The specific structure of the ester determines the functional attributes of the product, including release and liquidity. There are many possible structural variations which can impact upon the performance of esters. We have learned that the presence of a specific beta branching in the acid side of the molecule results in improved properties. While not wanting to be limited to one specific theory of application, we believe that highly branched esters are less soluble in the polycarbonate melt and because of their structure "tumble" out of the polymer to the interface between the mold and the plastic. This allows for efficient mold release, particularity if the ester is liquid at the temperature at which the molded plastic is removed from the mold.

The compounds of the current invention are specific branched esters conforming to the following structure;

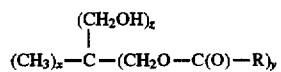

wherein:

R is:

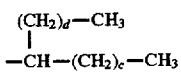

x is and integer ranging from 0 to 1;

z is an integer ranging from 0 to 3;

y is and integer ranging from 1 to 4, with the proviso that $x+y+z=4$;

c and d are independently integers ranging from 3 to 17.

PREFERRED EMBODIMENT

In a preferred embodiment c and d are each 3.
In another preferred embodiment c and d are each 4.
In another preferred embodiment c and d are each 5.
In another preferred embodiment c and d are each 6.
In another preferred embodiment c and d are each 7.
In another preferred embodiment c and d are each 8.
In still another preferred embodiment c and d are each 14.
In still another preferred embodiment c and d are each 17.

EXAMPLES

RAW MATERIALS

Guerbet Acids

Guerbet alcohols are oxidized into acids having the same regiospecific beta branched properties. This branching property present in the acid make products useful in the present invention.

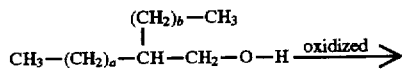

Guerbet Alcohol

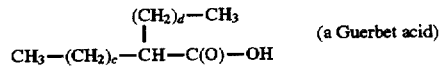   (a Guerbet acid)

Vista Chemical practices the oxidation of guerbet alcohols commercially. The values of c and d were actually determined by analysis and are not dependant upon trade name for meaning.

| Example | Commercial Name | c | d |
|---|---|---|---|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |
| 8 | Isocarb 40 | 17 | 17 |

Isocarb is a trademark of Vista.

Hydroxy Compound

Example 9

Pentaerythritol

Pentaerythritol is a commercially available tetra functional hydroxy compound conforming to the following structure:

Example 10

Another commercially available tri-functional hydroxy compound useful in the synthesis of compounds of the present invention conforms to the following structure:

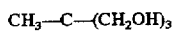

Ester Synthesis

The esterification reaction is carried out using an excess of hydroxy compound or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The ester is prepared by the esterification reaction as shown below:

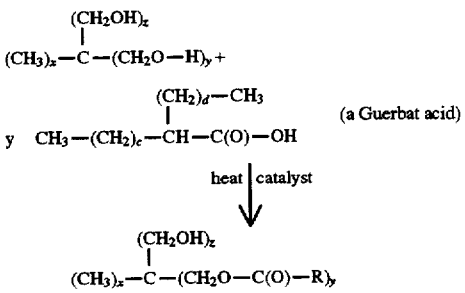

wherein;

x is and integer ranging from 0 to 1;

z is an integer ranging from 0 to 3;

y is and integer ranging from 1 to 4, with the proviso that $x+y+z=4$;

c and d are independently integers ranging from 3 to 17.

It should be clear that the value of z is determined by the amount of guerbet acid used relative to hydroxyl compound. If a 1:1 mole ratio (hydroxyl:acid) is used z will be 0. If a mole ratio of 1:0.3 (hydroxyl:acid) is used z will be 3.

General Procedure

To the specified number of grams of guerbet acid (examples 1–7) is added the specified number of grams of the specified hydroxyl compound. Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical. The products are clear liquids and are liquid to extraordinary temperatures. They exhibit outstanding lubrication properties and are outstanding viscosity index modifiers.

Example 11

To 171.0 grams of guerbet acid (examples 1) is added the 34.0 grams of the specified hydroxy compound (example 9). Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical.

Example 11 is repeated only this time the type and quantity of hydroxy compound and guerbet acid are substituted for the guerbet acid specified in Example 11.

|         | Hydroxy Compound |       | Guerbet Acid |       |
|---------|------------------|-------|--------------|-------|
| Example | Example          | Grams | Example      | Grams |
|         | Class 1          | x and z are 0; y is 4 | | |
| 11      | 9                | 34.0  | 1            | 171.0 |
| 12      | 9                | 34.0  | 2            | 199.0 |
| 13      | 9                | 34.0  | 3            | 227.0 |
| 14      | 9                | 34.0  | 4            | 255.0 |
| 15      | 9                | 34.0  | 5            | 283.0 |
| 16      | 9                | 34.0  | 6            | 311.0 |
| 17      | 9                | 34.0  | 7            | 479.0 |
| 18      | 9                | 34.0  | 8            | 592.0 |
|         | Class 2          | x is 1   z is 0 | y is 3 | |
| 19      | 10               | 39.0  | 1            | 171.0 |
| 20      | 10               | 39.0  | 2            | 199.0 |
| 21      | 10               | 39.0  | 3            | 227.0 |
| 22      | 10               | 39.0  | 4            | 255.0 |
| 23      | 10               | 39.0  | 5            | 283.0 |
| 24      | 10               | 39.0  | 6            | 311.0 |
| 25      | 10               | 39.0  | 7            | 479.0 |
| 26      | 10               | 39.0  | 8            | 592.0 |
|         | Class 3          | x is 0   z is 1 | y is 3 | |
| 27      | 9                | 25.0  | 1            | 171.0 |
| 28      | 9                | 25.0  | 2            | 199.0 |
| 29      | 9                | 25.0  | 3            | 227.0 |
| 30      | 9                | 25.0  | 4            | 255.0 |
| 31      | 9                | 25.0  | 5            | 283.0 |
| 32      | 9                | 25.0  | 6            | 311.0 |
| 33      | 9                | 25.0  | 7            | 479.0 |
| 34      | 9                | 25.0  | 8            | 592.0 |
|         | Class 4          | x is 1   z is 1 | y is 2 | |
| 35      | 10               | 30.0  | 1            | 171.0 |
| 36      | 10               | 30.0  | 2            | 199.0 |
| 37      | 10               | 30.0  | 3            | 227.0 |
| 38      | 10               | 30.0  | 4            | 255.0 |
| 39      | 10               | 30.0  | 5            | 283.0 |
| 40      | 10               | 30.0  | 6            | 311.0 |
| 41      | 10               | 30.0  | 7            | 479.0 |
| 42      | 10               | 30.0  | 8            | 592.0 |

Applications Information

The polycarbonates with which the present esters are effective lubricants include homopolycarbonates and copolycarbonates which are based, for example, on one or more of the following bisphenols: hydroquinone, resorcinol, dihydroxydiphenyls, bis-(hydroxyphenyl)-alkanes, bis-(hydroxyphenyl)-cycloalkanes, bis-(hydroxylphenyl)-sulphides, bis-(hydroxyphenyl)-ethers, bis-(hydroxylphenyl)-ketones, bis-(hydroxyphenyl)-sulphoxides, bis-(hydroxyphenyl)-sulphones and alpha, alpha-bis(hydroxyphenyl)-diisopropyl-benzenes, as well as their nuclear alkylated and nuclear-halogenated compounds.

Preferred aromatic polycarbonates are those which are based on one or more of the bisphenols mentioned as being preferred. Particularly preferred copolycarbonates are those based on 2,2-bis-(4,hydroxyphenyl)-propane and one of the other bisphenols mentioned as being particularly preferred. Further particularly preferred polycarbonates are those based solely on 2,2-bis-(4-hydroxyphenyl)-propane or 2,2-bis-(3,5-dimethyl-4-hydroxyphenyl)-propane.

The aromatic polycarbonates can be prepared in accordance with know processes, such as, but not limited to the melt trans-esterification process from bisphenols and diphenyl carbonate and the two-phase boundary process from bisphenols and phosgene, as described in the above mentioned literature.

The aromatic high-molecular weight polycarbonates can be branched due to the incorporation of small amounts, preferably of between 0.05 and 2.0 mol % (relative to diphenols employed), of trifunctional or more than trifunctional compounds, especially compounds with three of more phenolic hydroxyl groups.

Some examples of compounds with three or more than three phenolic hydroxyl groups which can be used are phloroglucinol, 4,6-dimethyl-2,4,6-tri-(4hydroxyphenyl)-heptane-2, 4,6-dimethyl-2,4,6-tri-(4-hydroxyphenyl)-heptane, 1,4,5-tri-(4-hydroxyphenyl)-benzene, 1,1,1-tri-(4-hydroxphenyl)-ethane, tri-(4-hydroxyphenyl)-phenylmethane, 2,2-bis-(4,4-bis-(4-hydroxyphenyl)-cyclohexyl)-propane, 2,4-bis-(4-hydroxyphenylisopropyl)-Phenol, 2,6-bis-(2-hydrox-5-methylbenzyl)-4-methyphenol, 2-(4-hydroxyphenol), 2-2,4dihydroxyphenyl)-propane, hexa (4-(4-hydroxyphenylisopropyl)phenyl)orthoterephthalic acid ester, tetra-(4-hydroxyphenyl)-methane and 1,4-bis-((4',4"-dihydroxytriphenyl)methyl)-benzene. Some of the other trifunctional compounds are 2,4-dihydroxybenzoic acid, trimesic acid, cyanuric chloride and 3,3-bis-(4-hydroxyphyenyl)-2oxo-2,3-dihydroindole.

The aromatic high-molecular polycarbonates should as a rule have mean weight-average molecular weight (M) of at least 10,000; especially of 10,000 to 200,000; preferably of 20,000 to 80,000; determined by measuring the relative viscosity in CH 2 Cl 2 at 25 degrees C. and a concentration of 0.5% by weight.

The thermoplastic polycarbonate compositions, using the lubricants of the present invention, find use in several high performance areas. Such examples of use for the polycarbonates of the present invention utilizing the lubricant include laser read compact recording discs, precision extrusion of polycarbonate sheets for use in greenhouses and in products safe for food contact like water and other beverage bottles, microwave wear, baby formula bottles, beer mugs, pitchers, and food storage containers and other similar high performance specialty applications.

The level of use of the polyesters of this invention in the polycarbonate is from about 0.25% to about 1.0%; preferably from about 0.1% to about 0.25% by weight of the total polycarbonate compositions.

Applications Data

Lexan 181, a product of General Electric, known for it's superior toughness and high molecular weight was chosen for the evaluation. To 99.5 parts of Lexan 181 was added 0.5 parts of the test compound. The mixture processed through a twin screw extruder, at a temperature of 300 Degrees C. and 15,000 psi. The resulting product was evaluated for clarity and for presence of lubricating agent on the surface, by using the Isopropanol Washing Procedure described below;

Isopropanol Washing Procedure

A 100 gram ⅛" inch thick piece of polycarbonate sheet was immersed in 400 ml of isopropanol in a 500 ml beaker. The immersion time was 8 hours. After the immersion time was complete, the polycarbonate was removed and the alcohol transferred to a pre-weighed distillation flask. The isopropanol was then distilled off. The flask was then placed in an oven at 100 C. overnight. The residue was then weight after cooling in a dessicator.

The polycarbonate sheet prepared using compound gave a extremely uniform highly clear sheet. The sheet was tested using the above washing procedure.

A polycarbonate sheet prepared using pentaerythritol tertastearate gave variation in the uniform of the sheet. This sheet was also tested using the above washing procedure.

The results are as follows:

|  | Residue in Mg. | Appearance |
|---|---|---|
| Example 16 | 10 | Clear liquid |
| Example 24 | 0 | N/A |
| Pentaerythritol Tetrastearate | 128 | yellowish powder |

I claim:

1. A compound which conforms to the following structure:

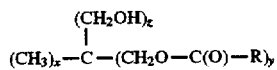

wherein:

R is:

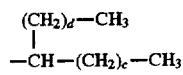

x is and integer ranging from 0 to 1;

z is an integer ranging from 0 to 3;

y is and integer ranging from 1 to 4, with the proviso that $x+y+z=4$;

c and d are independently integers ranging from 3 to 17.

2. A compound of claim 1 wherein c and d are each 3.
3. A compound of claim 1 wherein c and d are each 4.
4. A compound of claim 1 wherein c and d are each 5.
5. A compound of claim 1 wherein c and d are each 6.
6. A compound of claim 1 wherein c and d are each 7.
7. A compound of claim 1 wherein c and d are each 8.
8. A compound of claim 1 wherein c and d are each 14.
9. A compound of claim 1 wherein c and d are each 17.

* * * * *